(12) United States Patent
Palmer

(10) Patent No.: US 9,687,629 B1
(45) Date of Patent: Jun. 27, 2017

(54) AUTOMATIC GEL APPLYING CONTAINER FOR AN INTERMITTENT URINARY CATHETER

(71) Applicant: Cure Medical, LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 0 days.

(21) Appl. No.: 15/377,256

(22) Filed: Dec. 13, 2016

(51) Int. Cl.
*A61M 25/00* (2006.01)

(52) U.S. Cl.
CPC ...... *A61M 25/002* (2013.01); *A61M 25/0017* (2013.01)

(58) Field of Classification Search
CPC .................. A61M 25/0017; A61M 25/002
See application file for complete search history.

(56) References Cited

U.S. PATENT DOCUMENTS

| | | | |
|---|---|---|---|
| 4,204,527 A * | 5/1980 | Wu | A61M 25/002 600/575 |
| 4,622,033 A | 11/1986 | Taniguchi | |
| 6,053,905 A | 4/2000 | Daignault, Jr. et al. | |
| 6,090,075 A | 7/2000 | House | |
| 6,578,709 B1 | 6/2003 | Kavanagh et al. | |
| 6,602,244 B2 | 8/2003 | Kavanagh et al. | |
| 6,848,574 B1 | 2/2005 | Israelsson et al. | |
| 8,181,778 B1 | 5/2012 | van Groningen et al. | |

* cited by examiner

*Primary Examiner* — Leslie Deak
*Assistant Examiner* — Kai Weng
(74) *Attorney, Agent, or Firm* — SoCal IP Law Group LLP; Guy Cumberbatch; Steven C. Sereboff

(57) ABSTRACT

A rigid package or container for a catheter having catheter tube with a distal end and a proximal end, the proximal end being provided with a catheter outlet which may be used as a funnel or a connector. A main body is provided for holding the catheter, and a cap closes off the main body. A gel receptacle is positioned inside the main body, the gel receptacle being provided with a cavity for holding an amount of a lubricating agent. The gel receptacle includes a distal opening at a distal end thereof, and a proximal opening at a proximal end thereof, with the catheter tube extending therethrough. The gel receptacle is configured such that as the catheter is withdrawn therethrough a leading tip of the catheter is displaced so as to be immersed in the lubricating agent, thus automatically coating the leading tip.

20 Claims, 4 Drawing Sheets

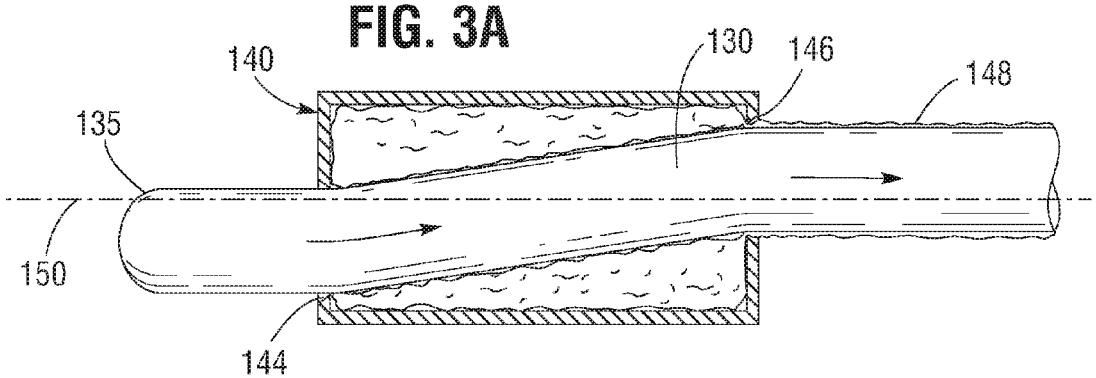
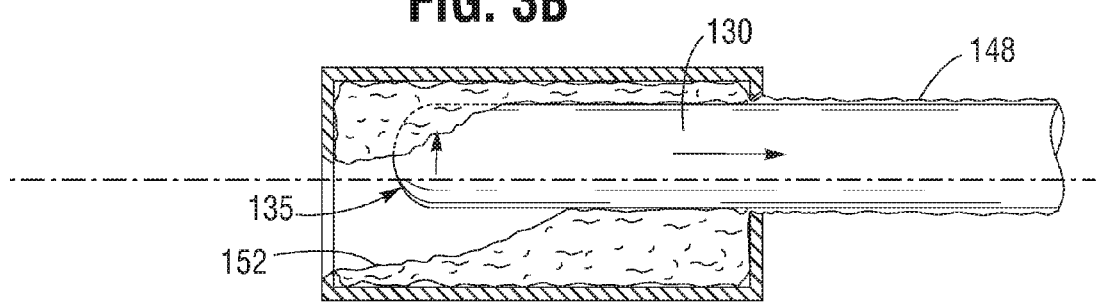
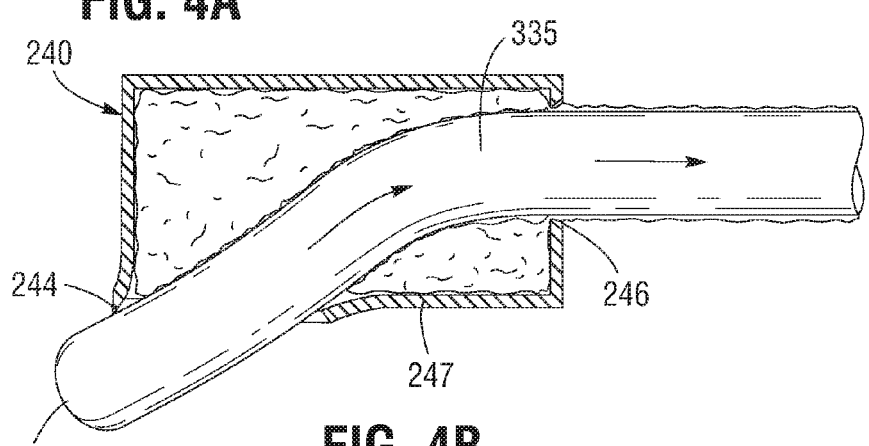
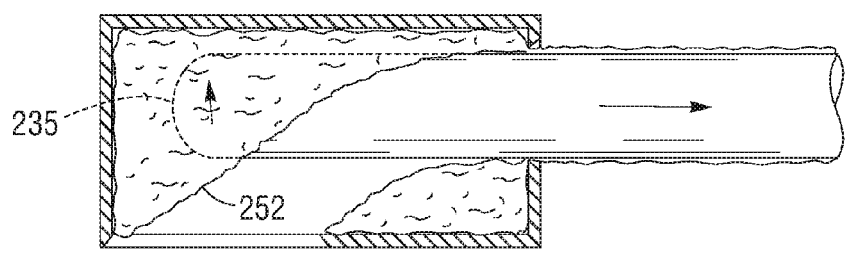

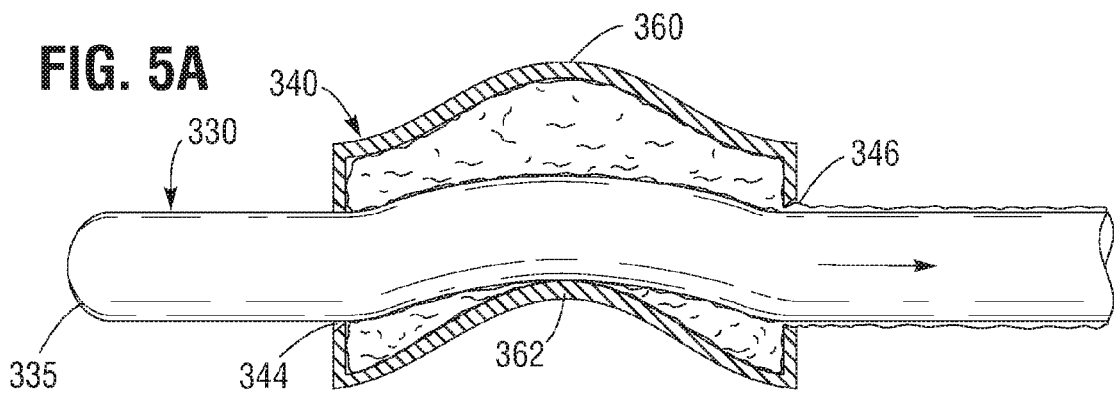
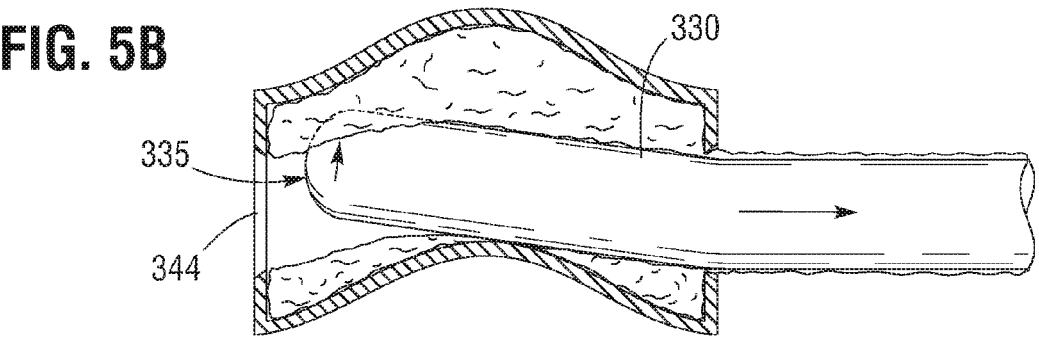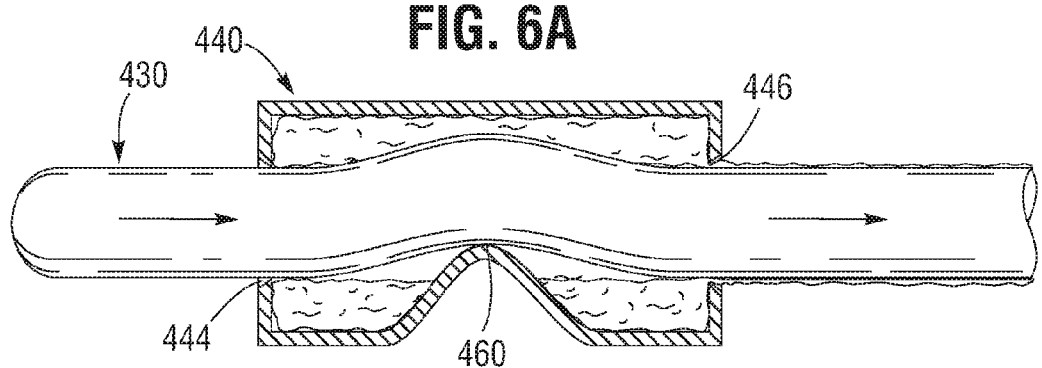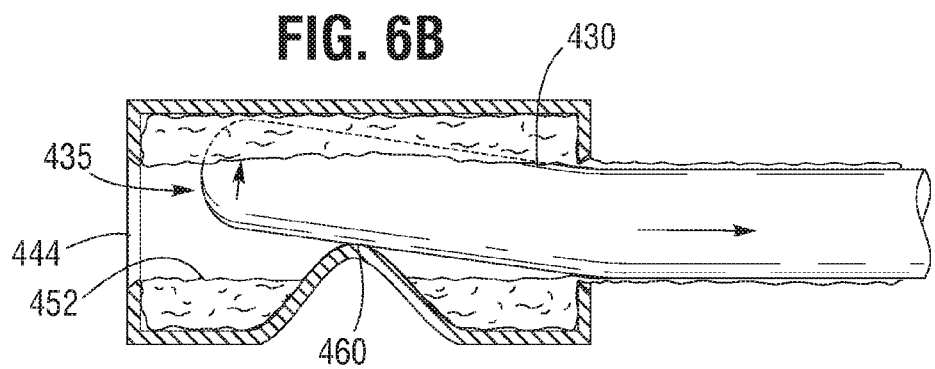

AUTOMATIC GEL APPLYING CONTAINER FOR AN INTERMITTENT URINARY CATHETER

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

Embodiments of the present invention relates to a sterile package housing a catheter, e.g., a urethral catheter, which can be used for (intermittent) self-catheterization by a patient.

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need, single use catheters have been developed to allow patients to perform self-catheterization. These catheters and their drainage tubes typically have a considerable length and are packaged in an elongated condition. It can require a considerable amount of space to store and transport enough catheters to accommodate a day long outing.

A gel container is used as a means to apply gel to a urology catheter upon withdrawal of the catheter from a package. The container holds the gel until needed and acts as a reservoir of gel for the catheter. U.S. Pat. Nos. 6,578,709 and 6,090,075 disclose packaged catheters which may be extended out of the package through a gel chamber so as to coat the leading end of the catheter. British patent application GB-A-2 319 507 also discloses a packaged catheter with a lubricant activating liquid therein. Likewise, U.S. Pat. No. 6,848,574 discloses a storage package with a catheter and a wetting liquid in the storage package. When needed, the leading end of the catheters disclosed above are pushed out of their containers, which may then be used as urine collectors.

Typically the catheter container is made of a flexible material like molded silicone. If the container is assembled into a rigid package there is no way for the user to manipulate the container to ensure adequate gel coverage of the distal (tip) end of the catheter.

The Cure Twist available from Cure Medical of Newport Beach, Calif. is a compact female length catheter packaged in a rigid tube package with an internal, flexible gel receptacle molded of silicone rubber. The gel receptacle holds lubricating gel in storage and applies it to the catheter tubing as the catheter is withdrawn from the package. U.S. Pat. No. 8,181,778 discloses such a rigid container for a catheter having a shortened tube with a leading end and a proximal end provided with a catheter outlet or connector. The user removes the catheter for use, either by joining the connector to a collection bag or other collection device or by simply using the catheter while sitting on the toilet. The catheter is lubricated and ready to use directly from the package.

SUMMARY OF THE INVENTION

Embodiments of the present invention seeks to provide an enhanced package for a (urethral) catheter, suitable for everyday use by a patient.

In accordance with embodiments of the present invention, a package is provided for a catheter that includes at least the following: a catheter having a catheter tube with a distal end and a proximal end, the proximal end being provided with a catheter connector; a main body for holding the catheter; a cap for closing off the main body, and a gel receptacle positioned inside the main body, the gel receptacle being provided with a cavity for holding an amount of gel-like lubricating agent, and including a distal opening at a distal end, and a proximal opening at a proximal end, the distal opening diameter corresponding to a catheter diameter, and the proximal opening diameter being larger than the catheter diameter.

The present invention is an improvement to the gel receptacle that ensures gel coverage of the tip section of the catheter to facilitate user comfort. The improvement can be done in a number of ways by use of a specially shaped gel container or by use of an internal feature in the gel container that tips the distal end of the catheter up into a reserve of gel just prior to exit from the gel container.

One aspect of the application is a catheter package comprising a rigid main body defining an inner space, and a cap provided at a proximal end of the main body which closes off a proximal end of the inner space. A catheter is received in the annular cavity of the main body, the catheter including a flexible catheter tube having a distal tip and at least one discharge opening proximate the distal tip, and a catheter outlet provided at a proximal end of the catheter tube. A gel receptacle is held in the inner space of the main body, the gel receptacle defining a cavity therein containing a lubricating agent. The gel receptacle has a distal opening at a distal end thereof with an inner diameter approximately the same as an outer diameter of the catheter tube, and a proximal opening at a proximal end thereof with an inner diameter greater than the outer diameter of the catheter tube. The catheter is stored in the inner space of the main body with the distal tip of the catheter tube positioned distal to the gel receptacle and the catheter outlet positioned proximal to the gel receptacle such that withdrawing the catheter proximally from the main body coats an exterior surface of the catheter tube with the lubricating agent. Further, the gel receptacle is configured such that the distal tip of the catheter tube displaces laterally from a straight line therethrough when it clears the distal opening to enhance lubricating agent coating of the distal tip.

A method of lubricating a catheter distal tip stored in a rigid package is also disclosed. The method includes the step of providing a catheter package comprising a rigid main body defining an inner space, and a cap provided at a proximal end of the main body which closes off a proximal end of the inner space. A catheter is received in the annular cavity of the main body, the catheter including a flexible catheter tube having a distal tip and at least one discharge opening proximate the distal tip, and a catheter outlet provided at a proximal end of the catheter tube. A gel receptacle is held in the inner space of the main body, the gel receptacle defining a cavity therein containing a lubricating agent, the gel receptacle having a distal opening at a distal end thereof with an inner diameter approximately the same as an outer diameter of the catheter tube, and a proximal opening at a proximal end thereof with an inner diameter greater than the outer diameter of the catheter tube. The catheter is stored in the inner space of the main body with the distal tip of the catheter tube positioned distal to the gel receptacle and the catheter outlet positioned proximal to the gel receptacle such that withdrawing the catheter proximally from the main body coats an exterior surface of the catheter tube with the lubricating agent. The method includes the step of withdrawing the catheter from the inner space of the main body such that the distal tip of the catheter tube automatically displaces laterally within the gel receptacle to enhance lubricating agent coating of the distal tip.

The gel receptacle may be generally tubular and the distal and proximal openings are offset from each other relative to a longitudinal axis through the gel receptacle so that the catheter must form a curve through the gel receptacle. The distal opening may be formed in a side wall of the gel receptacle and the proximal opening is formed in an end wall of the gel receptacle, or both the distal and proximal openings are formed in end walls of the gel receptacle. The distal and proximal openings are preferably positioned at opposite lateral sides of the longitudinal axis.

The gel receptacle may also be shaped so as to form an inward bulge on one side which extends into a straight line path for the catheter tube extending between the distal and proximal openings so as to deform the catheter tube through the gel receptacle. The gel receptacle may be generally tubular or serpentine shaped. In either case, both the distal and proximal openings are desirably centered in end walls of the gel receptacle.

Alternatively, the gel receptacle may include a spring finger which extends into a straight line path for the catheter tube extending between the distal and proximal openings so as to bias and deform the catheter tube through the gel receptacle.

BRIEF DESCRIPTION OF THE DRAWINGS

FIG. 3A is a schematic sectional view of a gel receptacle of the present application for use in a catheter container, and FIG. 3B shows a catheter leading end during withdrawal through the gel receptacle which has offset openings to ensure gel coating of the leading end;

FIG. 4A is a schematic sectional view of another alternative gel receptacle for use in a catheter container of the present application, and FIG. 4B shows a catheter leading end during withdrawal through the gel receptacle which also has offset openings to ensure gel coating of the leading end;

FIG. 5A is a schematic sectional view of a still further gel receptacle for a catheter container of the present application, and FIG. 5B shows a catheter leading end during withdrawal through the gel receptacle which has a serpentine configuration to ensure gel coating of the leading end;

FIG. 6A is a schematic sectional view of still another gel receptacle of the present application for use in a catheter container, and FIG. 6B shows a catheter leading end during withdrawal through the gel receptacle which has an internal fulcrum to ensure gel coating of the leading end;

DETAILED DESCRIPTION OF A PREFERRED EMBODIMENT

Description

Embodiments of the present invention aim to provide an easy to use and easy to carry solution for providing a medical device in the form of a catheter. As an example, the medical device is a urethral catheter that allows a patient or helper to empty the bladder of the patient. Embodiments of the present invention provide for a rigid package in which a catheter 30 such as a urethral catheter can be carried, and which is ready for use when taken from the package. Urethral catheter 30 may be used for intermittent self-catheterization.

More particularly, the sterile rigid catheter packages described herein contain a gel receptacle which is filled with a lubricant gel. The catheter is stored in a manner that its flexible distal tube is passed through the gel receptacle with a leading tip housed beyond the gel receptacle and within a closed distal end of the catheter. To operate, a user grasps a proximal end of the catheter and withdraws the catheter tube through the gel receptacle to coat it with lubricant gel. The present application discloses a number of different gel receptacles which may be used in a variety of such rigid catheter packages and which improve the coverage of gel on the leading tip of the catheter. As such, the application comprises both improved gel receptacles as well as improved packages with the gel receptacles therein.

Figure 1:
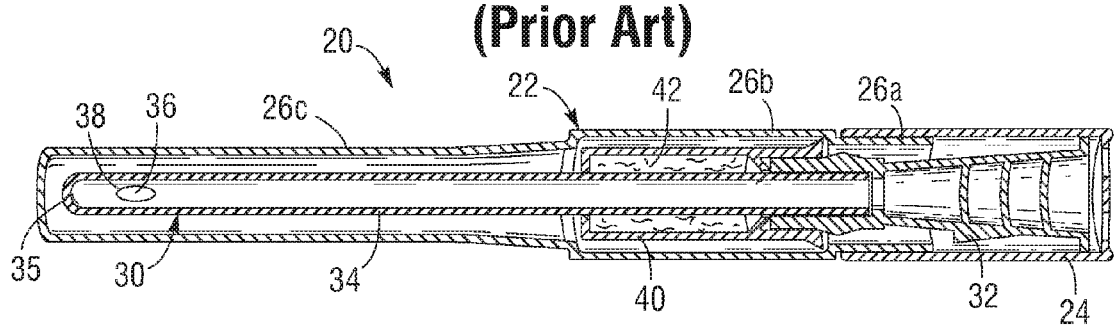
FIG. 1 is a longitudinal sectional view through a sterile container of the prior art for an intermittent urinary catheter.

FIG. 1 illustrates a cross sectional view of a prior art intermittent catheter container 20 such as shown in U.S. Pat. No. 8,181,778, with all elements assembled. Catheter container 20 includes a pen-like rigid and generally hollow tubular main body 22 which is closed off at a distal end thereof, and which can be closed off at a proximal, open end using cap 24. The rigid cap 24 can be attached to the main body 22 using various attachment/locking methods, such as a screw thread, a bayonet closure or a clamping arrangement. The cap 24 desirably has a plurality of openings (not shown) to permit the introduction of a sterilizing gas into the catheter package.

The cross-sectional view of main body 22 shows a proximal first part 26a, a middle second part 26b and distal third part 26c, which have respective diameters as described in U.S. Pat. No. 8,181,778. Preferably, first part 26a has a first inner diameter which is less than second inner diameter of second part 26b, and third part 26c has a third inner diameter which is less than second inner diameter of second part 26b. In other words, the middle second part 26b has a larger diameter than either of the proximal or distal parts.

As illustrated, a urethral catheter 30 is stored in a sterile condition within the main body 22 with the cap 24 on. At a proximal end thereof, catheter 30 is provided with a catheter outlet 32, which may be used as an outlet funnel or as a connector to attach the catheter 30 to a collection bag or other collection device. Catheter 30 includes a flexible catheter tube 34 provided with a rounded tip 35 on a distal end and one or more discharge openings 36 proximate the tip. Openings 36 are provided with rounded and or polished rims 38, such that the entry of urethral catheter tube 34 into the urethral tract of a patient is as comfortable as possible for the patient. The first part 26a of the main body receives the cap 24, the second part 26b holds a gel receptacle 40, and the third part 26c holds the elongated catheter tube 34 of the catheter 30.

The rigid nature of the container 20 and short length of the catheter 30 therein make the sterile package formed by the assembly highly portable and conveniently stored in a purse or even pocket.

The cap 24 contains the proximal outlet 32 of the catheter 30 and may be made of a transparent material, which allows inspection of the outlet 32 (which can, e.g., show size or other indicia, markings, etc.).

The dimensions of container 20 (or more specifically, the internal dimensions of main body 22 and cap 24) are adapted to allow storage of the entire catheter 30 (which may have varying dimensions). A length of the container 20 desirably corresponds closely to the length of catheter 30, and is preferably slightly greater than the length of catheter 30 so that the package closely surrounds the entire catheter 30. In accordance with embodiments, catheter 30 can have a length in a range of between about 10-15 cm, which makes catheter 30 especially suited for use with female patients.

Figure 2A:
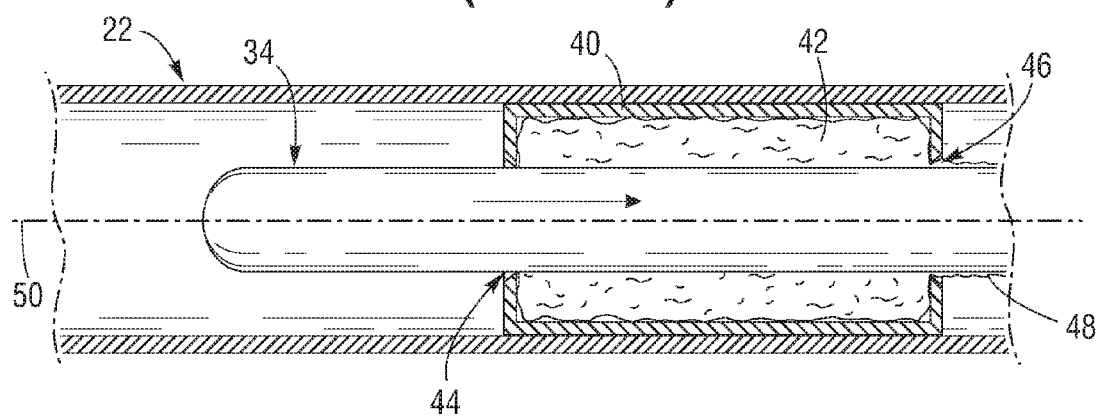
FIG. 2A is a schematic sectional view of a gel receptacle of the prior art catheter container of FIG. 1.

A gel receptacle 40 is provided and positioned in second part 26b of main body 22 as illustrated schematically in the enlarged cross-sectional view of FIG. 2A. Gel receptacle 40 is illustrated as a single generally tubular element provided with cavity 42 in which an amount of a gel-like lubricant agent is stored. As seen in FIG. 2A, gel receptacle 40 includes distal opening 44 at a distal end thereof, and proximal opening 46 at a proximal end thereof. Distal opening 44 has diameter corresponding generally to outer diameter of catheter tube 34, while proximal opening 46 has diameter slightly greater than the outer diameter of catheter tube 34. The first and proximal openings 44, 46 are aligned with each other along a longitudinal centerline 50 extending between the distal and proximal ends of the gel receptacle 40. When taking or otherwise removing catheter 30 in a proximal direction out of the package (to the right as indicated by movement arrow in FIG. 2A), a layer 48 of the gel-like lubricant extrudes through proximal opening 46 and is deposited on the outside surface of the catheter for use.

Figure 2B:
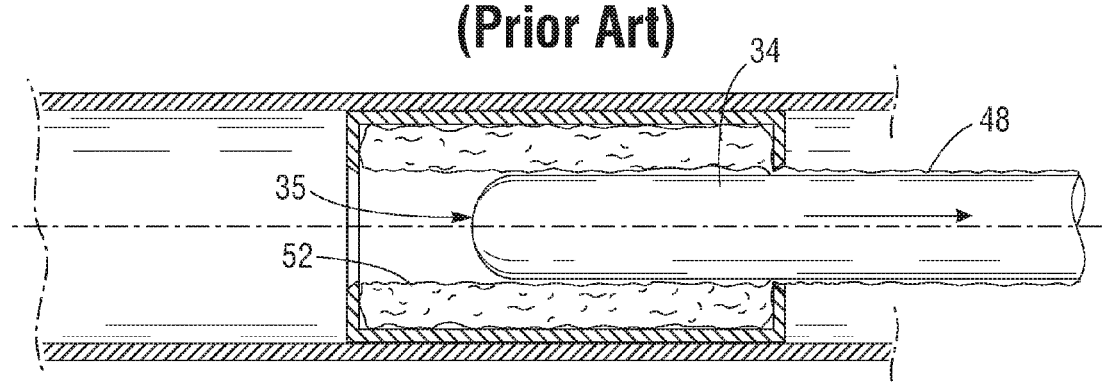
FIG. 2B shows a catheter leading end within the gel receptacle during withdrawal from the container.

FIG. 2B shows the catheter tube 34 retracted further in a proximal direction so that the leading tip 35 is within the gel receptacle 40. Because of its thixotropic properties, the gel adheres to the exterior sides of the catheter tube 34 as at 48, but often a tunnel 52 is formed in the gel material behind the catheter as it is pulled from the package. Consequently, the leading tip 35 of the catheter does not receive consistently good gel coverage. Application of lubricating gel to the leading tip 35 is important; the tip 35 being the first part of the catheter to be inserted into the urethra. If the very tip 35 of the catheter receives no gel it could make insertion more difficult for some users. In addition this problem is aggravated with longer lengths of catheters, for instance a male length catheter.

FIGS. 3A and 3B are schematic sectional views of a gel receptacle 140 of the present application through which a catheter tube of a catheter 130 passes. The gel receptacle 140 may be positioned in the catheter container 20 in place of the gel receptacle 40 shown and described above with reference to FIGS. 1 and 2A-2B, or in other configurations of catheter packaging which have a rigid outer housing and require withdrawal of the catheter in a proximal direction from the container. The gel receptacle 140 also has a cavity 142 filled with a lubricant gel, a distal opening 144 formed in a distal end wall, and a proximal opening 146 formed in a proximal end wall, both of through which the tube of the catheter 130 passes. As with the prior art, withdrawal of the catheter in a proximal direction pulls the leading tip 135 through the gel receptacle 140 to coat it with lubricating gel.

In contrast to the prior art, the openings 144, 146 are offset from each other, such as forming one or both offset relative to a longitudinal centerline 150 of the gel receptacle 140. In the illustrated embodiment, the distal opening 144 is offset in one lateral direction (down in the figure) from the longitudinal centerline 150, while the proximal opening 146 is offset in the opposite lateral direction (up in the figure). Consequently, the flexible tube of the catheter 130 deflects when inserted through the two openings 144, 146 to form the slightly serpentine shape of FIG. 3A.

FIG. 3B shows the catheter leading end 135 within the gel receptacle 140 during withdrawal therethrough, and a tunnel 152 thus formed behind it. However, due to the offset openings, once the leading end 135 is retracted past the distal opening 144 it tends to be displaced laterally as indicated by the movement arrow due to the inherently elastic nature of the catheter tube. This ensures the leading end 135 diverges from the tunnel 152 and into the lubricating gel, automatically coating the leading tip when the catheter is removed from the packaging.

FIG. 4A is a schematic sectional view of a gel receptacle 240 of another alternative catheter container of the present application. The gel receptacle 240 also has openings 244, 246 that are offset from each other. In contrast to the embodiment of FIG. 3A, a distal opening 244 is formed in a side wall 247 of the receptacle 240 rather than in a distal end wall. The proximal opening 246 is located in a proximal end wall and offset from a centerline in the opposite lateral direction from the side wall 247 to maximize the lateral offset distance between the two openings 244, 246.

FIG. 4B shows the catheter leading end 235 within the gel receptacle 240 during withdrawal of the tube of the catheter 230 in a proximal direction therethrough. As before, once the leading end 235 clears the distal opening 244 it tends to be displaced laterally upward as indicated by the movement arrow out of a gel tunnel 252 trailing the catheter and into the center of the gel receptacle 240. This movement is caused by the inherently elastic nature of the catheter tube and ensures the leading end 235 is coated with lubricating gel, automatically coating the leading tip when the catheter is removed from the packaging.

FIGS. 5A and 5B show a gel receptacle 340 of a still further catheter container which has a serpentine catheter pathway to ensure gel coating of the leading end. More particularly, the receptacle 340 curves upward in the middle to an apex 360 on one side and an inward bulge 362 on the other which extends into a straight line path for the tube of the catheter 330 extending between the distal and proximal openings 344, 346. As such, the tube of the catheter 330 is bowed upward from contact with the inward bulge 362. Distal and proximal openings 344, 346 are centered in each respective end wall, or may be offset toward the inward bulge 362. As the tube of the catheter 330 is withdrawn in a proximal direction such as in FIG. 5B, the leading tip 335 clears the distal opening 344 and is biased so as to displace laterally upward into the lubricating gel, automatically coating the leading tip when the catheter is removed from the packaging.

As mentioned above, the gel receptacle 340 may be supplanted into the prior art container 20 of FIG. 1. Of course, if the outer shape of the gel receptacle 340 is modified from the prior art receptacles, then some modification of the surrounding rigid housing would be required to receive the unconventional shape of the receptacle. The present application contemplates such modifications.

FIGS. 6A and 6B show a gel receptacle 440 which is generally tubular as before but has a crease in one side wall forming an internal fulcrum 460 to ensure gel coating of the leading end. As before, the flexible tube of the catheter 430 passes through distal and proximal end openings 444, 446. The fulcrum 460 comprises an inward bulge in one side wall that extends into a straight line path for the tube of the catheter 430 extending between the distal and proximal openings 444, 446 so as to deform the tube of the catheter 430 at that point. As a consequence, when the catheter 430 is withdrawn in a proximal direction as in FIG. 6B, the leading tip 435 clears the distal opening 444 and is biased laterally so as to displace it upward out of the trailing gel tunnel 452 and into the lubricating gel. This automatically coats the leading tip 435 when the catheter is removed from the packaging.

Figure 7A:
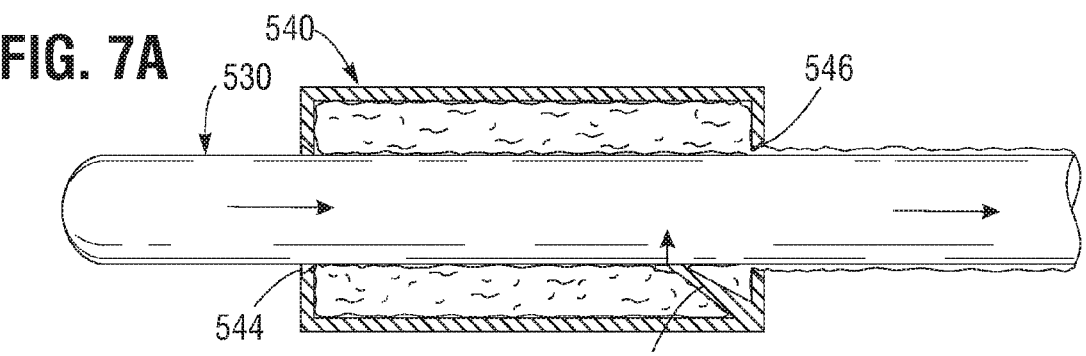
FIG. 7A is a schematic sectional view of a gel receptacle of another catheter container of the present application.
Figure 7B:
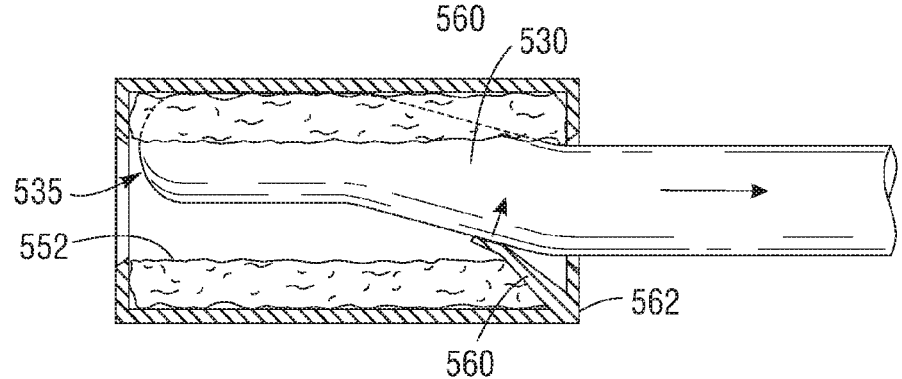
FIG. 7B shows a catheter leading end during withdrawal through the gel receptacle which has an internal spring finger to ensure gel coating of the leading end.

FIGS. 7A and 7B show a still further catheter container gel receptacle 540 of which has an internal spring finger 560 to ensure gel coating of the leading end. The finger 560 is shown angled radially and axially inward from a proximal corner 562 of the receptacle 540, though its placement and orientation may be altered. The length and angle of the finger 560 is such that it permits insertion of the tube of the catheter 530 in a distal direction when assembling the catheter container, and exerts a radially inward force to the catheter. When the catheter 530 is withdrawn, as shown in FIG. 7B, the leading tip 535 thereof eventually clears a distal opening 544. The bias force of the spring finger 560 displaces the leading tip 535 out of the trailing gel tunnel 552 and into the gel, thus coating the leading tip. This automatically coats the leading tip 535 when the catheter is removed from the packaging.

Figure 8A:
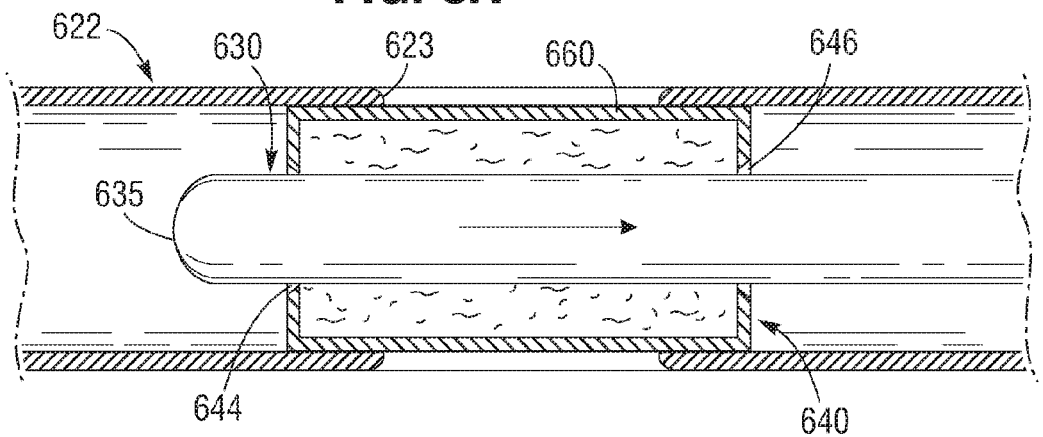
FIG. 8A is a schematic sectional view of another gel receptacle of the present application for a catheter container.
Figure 8B:
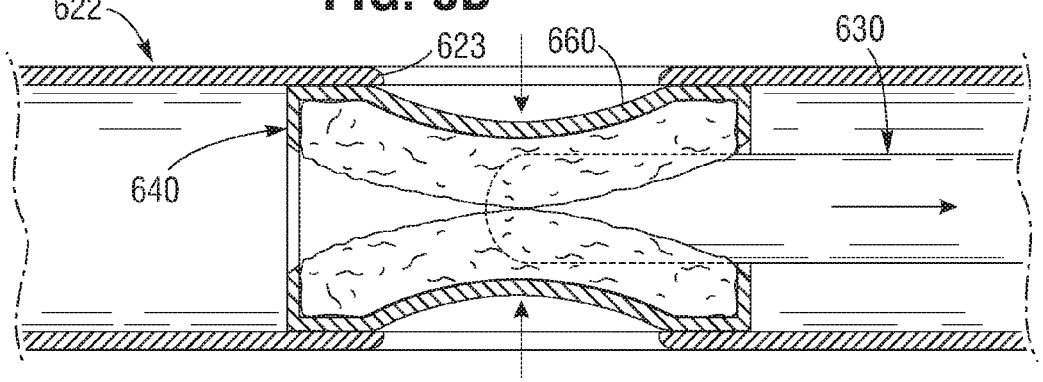
FIG. 8B shows a catheter leading end during withdrawal through the otherwise rigid gel receptacle which has a squeezable segment to ensure gel coating of the leading end.

In a slightly different configuration, FIGS. 8A and 8B show a gel receptacle 640 surrounded by a rigid outer container body 622. The gel receptacle 640 is tubular as before and includes distal and proximal openings 644, 646 preferably aligned along a centerline.

The body 622 has diametrically-opposed apertures 623 aligned with a mid-section of the receptacle 640. The receptacle 640 has side walls 660 that are deformable such that finger pressure on them through the apertures 623, as seen in FIG. 8B, closes the trailing gel tunnel 652 on the leading tip 635 of the tube of the catheter 630 to ensure gel coating of the leading end. The entire gel receptacle 640 may be made of the deformable material, such as being molded of silicone rubber, or just the side walls 660 thereof, or just a portion of the side walls. This embodiment serves to improve coating of the leading tip 635 as with the other embodiments, but requires a secondary action and is thus not automatic like the others.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A catheter package comprising:
   a) a rigid main body defining an inner space, and a cap provided at a proximal end of the main body which closes off a proximal end of the inner space;
   b) a catheter received in the annular cavity of the main body, the catheter including a flexible catheter tube having a distal tip and at least one discharge opening proximate the distal tip, and a catheter outlet provided at a proximal end of the catheter tube,
   c) a gel receptacle held in the inner space of the main body, the gel receptacle defining a cavity therein containing a lubricating agent, the gel receptacle having a distal opening at a distal end thereof with an inner diameter approximately the same as an outer diameter of the catheter tube, and a proximal opening at a proximal end thereof with an inner diameter greater than the outer diameter of the catheter tube; and
   wherein the catheter is stored in the inner space of the main body with the distal tip of the catheter tube positioned distal to the gel receptacle and the catheter outlet positioned proximal to the gel receptacle such that withdrawing the catheter proximally from the main body coats an exterior surface of the catheter tube with the lubricating agent, and wherein the gel receptacle is configured such that the distal tip of the catheter tube displaces laterally from a straight line therethrough when it clears the distal opening to enhance lubricating agent coating of the distal tip.

2. The catheter package of claim 1, wherein the gel receptacle is generally tubular and the distal and proximal openings are offset from each other relative to a longitudinal axis through the gel receptacle so that the catheter must form a curve through the gel receptacle.

3. The catheter package of claim 2, wherein the distal opening is formed in a side wall of the gel receptacle and the proximal opening is formed in an end wall of the gel receptacle.

4. The catheter package of claim 2, wherein both the distal and proximal openings are formed in end walls of the gel receptacle.

5. The catheter package of claim 4, wherein both the distal and proximal openings are positioned at opposite lateral sides of the longitudinal axis.

6. The catheter package of claim 1, wherein the gel receptacle is shaped so as to form an inward bulge on one side which extends into a straight line path for the catheter tube extending between the distal and proximal openings so as to deform the catheter tube through the gel receptacle.

7. The catheter package of claim 6, wherein the gel receptacle is generally tubular.

8. The catheter package of claim 6, wherein the gel receptacle is serpentine shaped.

9. The catheter package of claim 6, wherein both the distal and proximal openings are centered in end walls of the gel receptacle.

10. The catheter package of claim 1, wherein the gel receptacle includes a spring finger which extends into a straight line path for the catheter tube extending between the distal and proximal openings so as to bias and deform the catheter tube through the gel receptacle.

11. A method of lubricating a catheter distal tip stored in a rigid package, comprising:
   a) providing a catheter package comprising:
      i. a rigid main body defining an inner space, and a cap provided at a proximal end of the main body which closes off a proximal end of the inner space, a catheter being received in the annular cavity of the main body, the catheter including a flexible catheter tube having a distal tip and at least one discharge opening proximate the distal tip, and a catheter outlet provided at a proximal end of the catheter tube, and a gel receptacle held in the inner space of the main body, the gel receptacle defining a cavity therein containing a lubricating agent, the gel receptacle having a distal opening at a distal end thereof with an inner diameter approximately the same as an outer diameter of the catheter tube, and a proximal opening at a proximal end thereof with an inner diameter greater than the outer diameter of the catheter tube wherein the catheter is stored in the inner space of the main body with the distal tip of the catheter tube positioned distal to the gel receptacle and the catheter outlet positioned proximal to the gel receptacle such that withdrawing the catheter proximally from the main body coats an exterior surface of the catheter tube with the lubricating agent; and b) withdrawing the catheter from the inner space of the main body such that the distal tip of the catheter tube automatically displaces laterally within the gel receptacle to enhance lubricating agent coating of the distal tip.

12. The method of claim 11, and wherein the gel receptacle is configured such that the distal tip of the catheter tube displaces laterally from a straight line therethrough when it clears the distal opening.

13. The method of claim 11, wherein the gel receptacle is generally tubular and the distal and proximal openings are offset from each other relative to a longitudinal axis through the gel receptacle so that the catheter must form a curve through the gel receptacle.

14. The method of claim 12, wherein the distal opening is formed in a side wall of the gel receptacle and the proximal opening is formed in an end wall of the gel receptacle.

15. The method of claim 12, wherein both the distal and proximal openings are formed in end walls of the gel receptacle.

16. The method of claim 15, wherein both the distal and proximal openings are positioned at opposite lateral sides of the longitudinal axis.

17. The method of claim 11, wherein the gel receptacle is shaped so as to form an inward bulge on one side which extends into a straight line path for the catheter tube extending between the distal and proximal openings so as to deform the catheter tube through the gel receptacle.

18. The method of claim 17, wherein the gel receptacle is generally tubular.

19. The method of claim 17, wherein the gel receptacle is serpentine shaped.

20. The method of claim 11, wherein the gel receptacle includes a spring finger which extends into a straight line path for the catheter tube extending between the distal and proximal openings so as to bias and deform the catheter tube through the gel receptacle.

* * * * *